(12) United States Patent
Kaplan et al.

(10) Patent No.: US 7,014,848 B1
(45) Date of Patent: Mar. 21, 2006

(54) ENHANCED ANTI-TUMOR IMMUNITY

(75) Inventors: Johanne Kaplan, Sherborn, MA (US); Abraham Scaria, Framingham, MA (US)

(73) Assignee: Genzyme Corporation, Cambridge, MA (US)

(*) Notice: Subject to any disclaimer, the term of this patent is extended or adjusted under 35 U.S.C. 154(b) by 785 days.

(21) Appl. No.: 09/663,072

(22) Filed: Sep. 15, 2000

Related U.S. Application Data

(63) Continuation of application No. PCT/US99/06037, filed on Mar. 19, 1998.

(60) Provisional application No. 60/078,900, filed on Mar. 20, 1998.

(51) Int. Cl.
*A61K 39/00* (2006.01)

(52) U.S. Cl. .................. 424/93.21; 424/184.1

(58) Field of Classification Search ............. 424/93.21, 424/93.71, 325, 366, 372, 455, 236.1, 185.1, 424/192.1, 18, 288.1, 184.1; 514/44; 435/69.3
See application file for complete search history.

(56) References Cited

U.S. PATENT DOCUMENTS

| | | | |
|---|---|---|---|
| 5,633,234 A | | 5/1997 | August et al. |
| 5,728,388 A | * | 3/1998 | Terman .................. 424/236.1 |
| 5,856,180 A | | 1/1999 | Granucci |

FOREIGN PATENT DOCUMENTS

| | | | |
|---|---|---|---|
| WO | WO94/28113 | * | 12/1994 |
| WO | WO 97/10002 | | 3/1997 |
| WO | WO 97/19169 | | 5/1997 |

OTHER PUBLICATIONS

Riott et al (1996, Immunology, 19.8-9).*
Larsen, C.P. et al., "Migration and maturation of Langerhans cells in skin transplants and explants", Journal of Experimental Medicine, Nov. 1990, 172:1483-1493.
Maraskovsky, E. et al., "Dramatic Increase in the numbers of functionally mature dendritic cells in Flt3 ligand-treated mice: multiple dedritic cell subpopulations identifed", Journal of Experimental Medicine, Nov. 1996, 184(5):1953-1962.
Siena, S. et al., "Massive ex vivo generation of functional dendritic cells from mobilized CD34+ blood progenitors for anticancer therapy", Experimental Hematology, 1995, 23: 1463-1471.
Wan, Y. et al., "Dendritic cells transduced with an adenoviral vector encoding a model tumor-associated antigen for tumor vaccination", Human Gene Therapy, Jul. 1997, 8:1355-1363.

Specht et al., "Dendritic Cells Retrovirally Transduced with a Model Antigen Gene Therapeutically Effective Against Established Pulmonary Metastases", The Journal of Experimental Medicine, Oct. 1997, 186(8):1213-1221.
Reeves et al., "Retroviral Transduction of Human Dendritic Cells with a Tumor-Associated Antigen Gene", Cancer Research, Dec. 1996, 56:5672-5677.
Young et al., "Dendritic Cells as Adjuvants for Class I Major Histocompatibility Complex-restricted Antitumor Immunity", Journal of Experimental Medicine, Jan. 1996, 183:7-11.
de Zoeten, E.F. et al., "Resistance to Melanoma in Mice Immunized with Semiallogeneic Fibroblasts Transfected with DNA from Mouse Melanoma Cells", The Journal of Immunology, Mar. 1998, 160:2915-2922.
Cavallo, F. et al., "Protective and curative potential of vaccination with interleukin-2-gene-transfected cells from a spontaneous mouse mammary adenocarcinoma", Cancer Research, Nov. 1993, 53:5067-5070.
Russell, S.J. et al., "Decreased tumorigenicity of a transplantable rat sarcoma following transfer and expression of an IL-2-cDNA", International Journal of Cancer, 1991, 47:244-251.
Chakravarty, P.K. et al., "Tumorigenicity of interleukin-2 (IL-2)-cDNA-transfected L1210 lymphoma and its in vivo variants is modulated by changes in IL-2 expression: potential therapeutic implications", Cancer Immunology Immunotherapy, 1992, 35:347-354.
Hui, K.M., et al., "Tumor Rejection Mediated by Transfection with Allongeneic Class I Histocompatibility Gene", The Journal of Immunology, Dec. 1989, 143(11):3835-3843.
Ostrand-Rosenberg, S. et al., "Rejection of Mouse Sarcoma Cells After Transfection of MHC Class II Genes", The Journal of Immunology, May 1990, 144(10):4068-4071.
Nabel, G.J. et al., "Immune response in human melanoma after transfer of an allogeneic class I major histocompatibility complex gene with DNA-liposome complexes", Proc. National Academy of Science, Dec. 1996, 93:15388-15393.
Pershwa, M.V. et al., "Generation of Primary Peptide-Specific CD8+ Cytotoxic T-Lymphocytes In Vitro Using Allogeneic Dendritic Cells", Cell Transplantation, 1998, 7(1):1-9.
Dietz and Vuk-Pavlovic, "High Efficiency Adenovirus-Mediated Gene Transfer to Human Dendritic Cells", Blood, Jan. 1998, 91(2):392-398.
Doll, R. et al., "Adenoviral Infection of Human Dendritic Cells for use as Antitumor Vaccines", Cancer Gene Therapy, Nov. 1997, 4(6):S51-S52.

* cited by examiner

*Primary Examiner*—Misook Yu

(57) ABSTRACT

The present invention provides methods for inducing an antigen-specific immune response by administering allogeneic antigen-presenting cells to a subject. In another aspect, an effective amount of autologous antigen-presenting cells are co-administered to a subject.

12 Claims, 7 Drawing Sheets

ENHANCED ANTI-TUMOR IMMUNITY

CROSS-REFERENCE TO RELATED APPLICATION

This application is a continuation of international application number PCT US99/06037, filed 19 Mar. 1999.

This application claims priority under 35 U.S.C. §119(e) to U.S. Provisional Application No. 60/078,900, filed Mar. 20, 1998, the contents of which are hereby incorporated by reference into the present disclosure.

TECHNICAL FIELD

This invention is in the field of molecular immunology and medicine. In particular, methods of inducing an antigen-specific immune response are provided.

BACKGROUND

In spite of numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Failure occurs either because the initial tumor is unresponsive, or because of recurrence due to regrowth at the original site and/or metastases.

Cellular immunotherapy is emerging as a technologically and intellectually compelling anti-cancer treatment. The generation of an immune response against tumors has been demonstrated in several animal models and has been inferred from reports of spontaneous tumor regression in man (Stotter and Lotze (1990) *Cancer Cells* 2:44–55). Cytotoxic T-lymphocyte (CTL) responses can be directed against antigens specifically presented by tumor cells, both in vivo and in vitro, without the need for prior knowledge of the molecular mechanism by which the tumor arose. In animal models, established tumors can be eradicated by the adoptive transfer of educated T-cells that are specifically immune to the malignant cells (Beun et al. (1994) *Immunol. Today* 15:11–15).

DISCLOSURE OF THE INVENTION

In the most general aspect, the present invention provides a method of inducing an antigen-specific immune response in a subject by administering to that subject an effective amount of an allogeneic APC. In one embodiment, method further comprises administering an effective amount of an autologous APC. The APCs are administered under conditions that provoke an antigen specific immune response in the subject. The autologous APC, such as dendritic cells, will present antigen to cytotoxic T lymphocytes and elicit an antigen-specific response. The allogeneic APC, most suitably universal APCs (defined below) which also can be dendritic cells, will traffic to the same areas as the autologous cells, but will elicit a strong reaction from alloreactive T lymphocytes resulting in the local release of stimulatory cytokines that amplify the anti-antigen response and promote destruction of the antigen-expressing cells, such as tumor cells.

MODES FOR CARRYING OUT THE INVENTION

Figure 1:
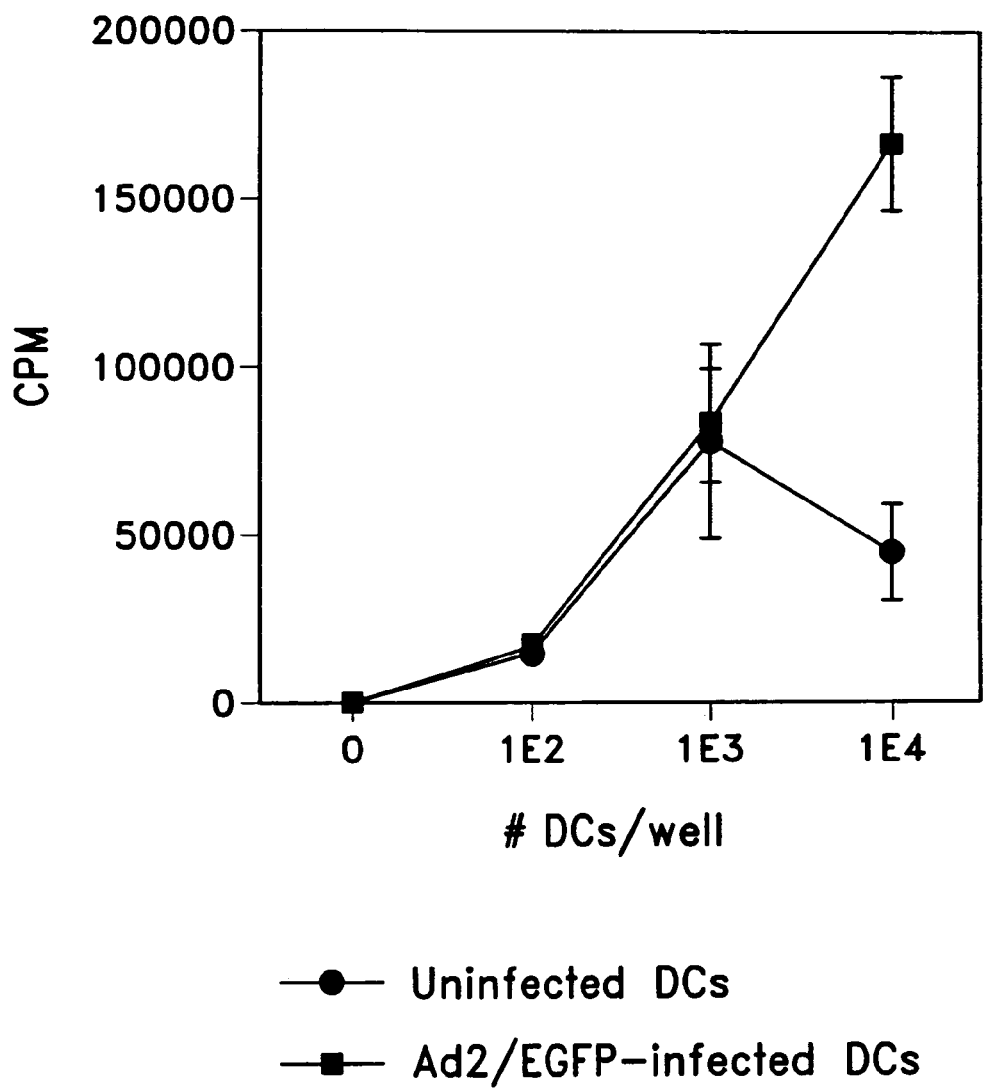
FIG. 1 shows induction of a mixed lymphocyte reaction (MLR) by dendritic cells. Varying numbers of bone-marrowed derived C57BL/6 dendritic cells (DCs) were used to stimulate allogeneic allogeneic BALB/c T lymphocytes. The DCs were either unifected or infected with adenovirus vectors. The level of proliferation induced was measured by tritiated thymidine incorporation after 5 days of culture. An overall dose-dependent stimulation was observed with increasing numbers DCs and the stimulatory activity of Ad-transfected DCs was equal or greater to that of uninfected DCs.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention will employ, unless otherwise indicated, conventional techniques of molecular biology, microbiology, cell biology, immunology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel et al. eds., (1987)); the series METHODS IN ENZYMOLOGY (Academic Press, Inc.); ANTIBODIES: A LABORATORY MANUAL (E. Harlow and D. Lane eds (1988)); PCR 2: A PRACTICAL APPROACH (M. J. MacPherson, B. D. Hames and G. R. Taylor eds. (1995)) and ANIMAL CELL CULTURE (R. I. Freshney, ed. (1987)).

Definitions

As used herein, certain terms may have the following defined meanings.

As used in the specification and claims, the singular form "a", "an" and "the" include plural references unless the context clearly dictates otherwise. For example, the term "a cell" includes a plurality of cells, including mixtures thereof.

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

The term "genetically modified" means containing and/or expressing a foreign gene or nucleic acid sequence which in turn, modifies the genotype or phenotype of the cell or its progeny. In other words, it refers to any addition, deletion or disruption to a cell's endogenous nucleotides.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1α), interleukin-11 (IL-11), MIP-1α, leukemia inhibitory factor (LIF), c-kit ligand, thrombopoietin (TPO) and flt3 ligand. The present invention also includes culture conditions in which one or more cytokine is specifically excluded from the medium. Cytokines are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the invention.

The terms "antigen-presenting cells" or "APCs" includes both intact, whole cells as well as other molecules which are capable of inducing the presentation of one or more antigens, preferably in association with class I MHC molecules. Examples of suitable APCs are discussed in detail below and include, but are not limited to, whole cells such as macrophages, dendritic cells, B cells; purified MHC class I molecules complexed to β2-microglobulin; and foster antigen presenting cells.

Dendritic cells (DCs) are potent antigen-presenting cells (APCs). It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC") class I or II protein on the surface of APCs. This interaction is necessary, but not sufficient, for T cell activation to occur. In fact, without the second type of signals, the first type of signals can result in T cell anergy. The second type of signals, called co-stimulatory signals, is neither antigen-specific nor MHC-restricted, and can lead to a full proliferation response of T cells and induction of T cell effector functions in the presence of the first type of signals. As used herein, "dendritic cell" is to include, but not be limited to a pulsed dendritic cell, a foster antigen presenting cell or a dendritic cell hybrid.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1α), interleukin 11 (IL-11), MIP-1α, leukemia inhibitory factor (LIF), c-kit ligand, thrombopoietin (TPO) and flt3 ligand. The present invention also includes culture conditions in which one or more cytokines is specifically excluded from the medium. Cytokines are commercially available from several vendors such as, for example, Genzyme (Framingham, Mass.), Genentech (South San Francisco, Calif.), Amgen (Thousand Oaks, Calif.), R&D Systems and Immunex (Seattle, Wash.). It is intended, although not always explicitly stated, that molecules having similar biological activity as wild-type or purified cytokines (e.g., recombinantly produced or biologically equivalent variants thereof) are intended to be used within the spirit and scope of the invention.

The terms "major histocompatibility complex" or "MHC" refers to a complex of genes encoding cell-surface molecules that are required for antigen presentation to T cells and for rapid graft rejection. In humans, the MHC complex is also known as the HLA complex. The proteins encoded by the MHC complex are known as "MHC molecules" and are classified into class I and class II MHC molecules. Class I MHC molecules include membrane heterodimeric proteins made up of an chain encoded in the MHC associated noncovalently with β2-microglobulin. Class I MHC molecules are expressed by nearly all nucleated cells and have been shown to function in antigen presentation to CD8+ T cells. Class I molecules include HLA-A, -B, and -C in humans. Class I molecules generally bind peptides 8–10 amino acids in length. Class II MHC molecules also include membrane heterodimeric proteins consisting of noncovalently associated α and β chains. Class II MHC are known to participate in antigen presentation to CD4+ T cells and, in humans, include HLA-DP, -DQ, and DR. Class II molecules generally bind peptides 12–20 amino acid residues in length. The term "MHC restriction" refers to a characteristic of T cells that permits them to recognize antigen only after it is processed and the resulting antigenic peptides are displayed in association with either a self class I or class II MHC molecule. Methods of identifying and comparing MHC are well known in the art and are described in Allen et al. (1994) *Human Imm.* 40:25–32; Santamaria et al. (1993) *Human Imm.* 37:39–50; and Hurley et al. (1997) *Tissue Antigens* 50:401–415.

"Host cell" is intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be procaryotic or eucaryotic, and include but are not limited to bacterial cells, yeast cells, animal cells, and mammalian cells, e.g., murine, rat, simian or human. An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody (as defined above) and its binding partner or ligand.

A native antigen is a polypeptide, protein or a fragment containing an epitope, which induces an immune response in the subject.

An "effective amount" is an amount sufficient to effect beneficial or desired results. An effective amount can be administered in one or more administrations, applications or dosages. The polynucleotides of the present invention may be administered or applied transdermally, orally, subcutaneously, intramuscularly, intravenously or parenterally. For purposes of this invention, an effective amount of the polynucleotides is that amount which provokes an antigen-specific immune response in the subject.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules.

"Oligonucleotide" refers to polynucleotides of between about 5 and about 100 nucleotides of single- or double-stranded DNA. Oligonucleotides are also known as oligomers or oligos and may be isolated from genes, or chemically synthesized by methods known in the art. A "primer" refers to an oligonucleotide, usually single-stranded, that provides a 3'-hydroxyl end for the initiation of enzyme-mediated nucleic acid synthesis.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinycytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentylnyluracil and 2,6-diaminopurine. The use of uracil as a substitute for thymine in a deoxyribonucleic acid is also considered an analogous form of pyrimidine. By way of example only and not to limit this invention, the polynucleotides encode a peptide, a ribozyme or an antisense sequence.

"PCR primers" refer to primers used in "polymerase chain reaction" or "PCR," a method for amplifying a DNA base sequence using a heat-stable polymerase such as Taq polymerase, and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce exponential and highly specific amplification of the desired sequence. (See, e.g., PCR 2: A PRACTICAL APPROACH, supra). PCR also can be used to detect the existence of the defined sequence in a DNA sample.

The terms "protein", "oligopeptide", "polypeptide" and "peptide" are used interchangeably to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modification known in the art.

The term "culturing" refers to the in vitro propagation of cells or organisms on or in media of various kinds. It is understood that the descendants of a cell grown in culture may not be completely identical (either morphologically, genetically, or phenotypically) to the parent cell. By "expanded" is meant any proliferation or division of cells.

A "subject" is a vertebrate, preferably a mammal, more preferably a human. Mammals include, but are not limited to, murines, simians, humans, farm animals, sport animals, and pets.

A "composition" is intended to mean a combination of active agent and another compound or composition, inert (for example, a detectable agent or label) or active, such as an adjuvant. In one particular aspect, a composition of this invention comprises the transduced APC and a pharmaceutically acceptable carrier suitable for administration to the subject. A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

"Co-stimulatory molecules" are involved in the interaction between receptor-ligand pairs expressed on the surface of antigen presenting cells and T cells. Research accumulated over the past several years has demonstrated convincingly that resting T cells require at least two signals for induction of cytokine gene expression and proliferation (Schwartz R. H. (1990) *Science* 248:1349–1356 and Jenkins M. K. (1992) *Immunol. Today* 13:69–73). One signal, the one that confers specificity, can be produced by interaction of the TCR/CD3 complex with an appropriate MHC/peptide complex. The second signal is not antigen specific and is termed the "co-stimulatory" signal. This signal was originally defined as an activity provided by bone-marrowderived accessory cells such as macrophages and dendritic cells, the so called "professional" APCs. Several molecules have been shown to enhance co-stimulatory activity. These are heat stable antigen (HSA) (Liu Y. et al. (1992) *J. Exp. Med.* 175:437–445); chondroitin sulfate-modified MHC invariant chain (Ii-CS) (Naujokas M. F. et al. (1993) *Cell* 74:257–268); intracellular adhesion molecule 1 (ICAM-1) (Van Seventer, G. A. (1990) *J. Immunol.* 144:4579–4586); and B7-1 and B7-2/B70 (Schwartz R. H. (1992) *Cell* 71:1065–1068). One exemplary receptor-ligand pair is the B7 co-stimulatory molecule on the surface of APCs and its counter-receptor CD28 or CTLA-4 on T cells (Freeman et al. (1993) *Science* 262:909–911; Young et al. (1992) *J. Clin. Invest.* 90:229; and Nabavi et al. (1992) *Nature* 360:266–268). Other important co-stimulatory molecules are CD40, CD54, CD80, CD86. As used herein, the term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7, or other co-stimulatory molecule(s) on an antigen-presenting matrix such as an APC, fragments thereof (alone, complexed with another molecule(s), or as part of a fusion protein) which, together with peptide/MHC complex, binds to a cognate ligand and results in activation of the T cell when the TCR on the surface of the T cell specifically binds the peptide. Co-stimulatory molecules are commercially available from a variety of sources, including, for example, Beckman Coulter. It is intended, although not always explicitly stated, that molecules having similar biological activity as wild-type or purified co-stimulatory molecules (e.g., recombinantly produced or muteins thereof) are intended to be used within the spirit and scope of the invention.

The term "modulate an immune response" includes inducing (increasing, eliciting) an immune response; and reducing (suppressing) an immune response. An immunomodulatory method (or protocol) is one that modulates an immune response in a subject.

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected (measured), after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody). Immune effector cells specific for the antigen can be detected any of a variety of assays known to those skilled in the art, including, but not limited to, FACS, or, in the case of CTLs, $^{51}$Cr-release assays, or $^3$H-thymidine uptake assays.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

The present invention provides a method for provoking antigen-specific immune responses, and in particular, immune responses against tumor antigens. In particular, this invention exploits the fact that alloreactivity (reactivity against foreign MHC antigens) is a universally strong immune reaction leading to the activation of CD4$^+$ and CD8$^+$ T lymphocytes. Dendritic cells (DC) which display high densities of MHC class I and class II antigens, are especially potent stimulators of alloreactive T cells which has been confirmed in a mixed lymphocyte reaction (See FIG. 1). In this invention, the ability of DCs to elicit potent alloreactivity is harnessed to promote the activation of tumor-specific T lymphocytes which are stimulated concurrently with autologous, MHC-compatible DCs expressing a relevent tumor-associated antigen(s) (TAA). In a particular aspect of this invention, the APC are dendritic cells, which are purified from the same and unrelated subject. Alternatively, more primitive cells of the hematopoietic lineage are isolated and cultured in appropriate growth factors which enrich for a population of dendritic cells. The release of stimulatory cytokines by high frequency alloreactive T lymphocytes supports and amplifies the weaker response of tumor-specific T lymphocytes. In one embodiment, only allogeneic cells are administered to the subject to induce the immune response. In a preferred embodiment, the allogeneic APCs are loaded with with the antigen of interest, i.e., against which the immune response is to be raised.

The method of this invention comprises co-administering to a subject allogeneic and autologous antigen presenting cells (APCs), wherein the autologous APC express the antigen against which the immune response is raised. In the context of cancer gene therapy, the invention provides a means to amplify the host immune response against an antigen, and in particular, a TAA. In one aspect and using the methods known in the art and described briefly below, the APC are purified, autologous APC are purified from the subject and the allogeneic APC are purified from an unrelated subject and expressing the antigen of interest which are then administered intravenously or intradermally. In a further aspect, these APC are transduced with a polynucleotide that codes for the antigen of interest, e.g., gp100, MART1, MUC-1. The polynucleotide coding for the antigen may be from the same or similar species, for example the gene coding for the human gp100 can be transduced into the autologous APC.

The polynucleotides encoding TAAs of this invention can be, in one embodiment, previously characterized tumor-associated antigens such as gp100 (Kawakami et al. (1997) *Intern. Rev. Immunol.* 14:173–192), MUC-1 (Henderson et al. (1996) *Cancer Res.* 56:3763–3770), MART-1 (Kawakami, et al. (1994) *Proc. Natl. Acad. Sci.* 91:3515–3519; Kawakami et al. (1997) *Intern. Rev. Immunol.* 14:173–192; Ribas, et al. (1997) *Cancer Res.* 57:2865–2869), HER-2/neu (U.S. Pat. No. 5,550,214), MAGE (PCT/US92/04354) HPV16, 18E6 and E7 (Ressing et al. (1996) *Cancer Res.* 56 (1):582–588; Restifo (1996) *Current Opinion in Immunol.* 8:658–663; Stern, (1996) *Adv. Cancer Res.* 69:175–211; Tindle, et al. (1995) *Clin. Exp. Immunol.* 101:265–271; van Driel, et al. (1996) *Annals of Medicine* 28:471–477) CEA (U.S. Pat. No. 5,274,087), PSA (Lundwall, A. (1989) *Biochem. Biophys. Research Communications* 161:1151–59), prostate membrane specific antigen (PSMA) (Israeli, et al. (1993) *Cancer Research* 53:227–30), tyrosinase (U.S. Pat. Nos. 5,530,096 and 4,898,814; Brichard, et al. (1993) *J. Exp. Med.* 178:489–49); tyrosinase related proteins 1 or 2 (TRP-1 and TRP-2), NY-ESO-1 (Chen, et al. (1997) *Proc. Natl. Acad. Sci. U.S.A.* 94:1914–18), or the GA733 antigen (U.S. Pat. No. 5,185,254). Sequences for exemplary antigens are provided in FIGS. 1 through 4. The human and murine MUC1 coding sequences are provided under Genbank Accession No. M35093 and M64928.

In a yet further aspect of this invention, the cells can be transduced with a polynucleotide coding for a yet unidentified antigen which is identified and sequenced using methods described herein.

The cells are transduced using a "gene delivery vehicle" which is any agent that can carry inserted polynucleotides into a host APC. Examples of gene delivery vehicles are liposomes, viruses, such as baculovirus, adenovirus, and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

Thus, presentation of the antigens such as tumor associated antigens by the APCs elicits a strong immune response resulting in destruction of tumor cells by antigen-specific immune effector cells such as cytotoxic T lymphocytes (CTLs). The induction of the CTL response is one method to assay for a positive response to the therapy and a means to confirm the biological activity of new factors useful in the methods of this invention. The presence of a large number of T-cells in tumor has been correlated with a prognostically favorable outcome in some cases (Whiteside and Parmiani, (1994) *Cancer Immunol. Immunother.* 39:15–21. Woolley, et al. (1995) *Immunology* 84:55–63, has shown that implantation of polyurethane sponges containing irradiated tumor cells can efficiently trap anti-tumor CTLs (4-times greater than lymph fluid, 50-times greater than spleen or peripheral blood). Following activation with T-cell cytokines in the presence of their appropriately presented recognition antigen, TILs proliferate in culture and acquire potent anti-tumor cytolytic properties. Weidmann, et al. (1994) *Cancer Immunol. Immunother.* 39:1–14. Assays to determine T cell response are well known in the art and any method that will compare T cell number and activity prior to and subsequent to therapy can be utilized.

Several different techniques have been described which lead to the expression of antigen in the cytosol of APCs, such as DCs. These include (1) the introduction into the APCs of RNA isolated from tumor cells, (2) infection of APCs with recombinant vectors to induce endogenous expression of antigen, and (3) introduction of tumor antigen into the DC cytosol using liposomes. (See Boczkowski, D., et al. (1996) *J. Exp. Med.* 184:465–472; Rouse, et al., (1994) *J. Virol.* 68:5685–5689; and Nair, et al. (1992) *J. Exp. Med.* 175:609–612). Paglia et al. (*J. Exp. Med.* 183:317–322 (1996)) has shown that APC incubated with whole protein in vitro were recognized by MHC class I-restricted CTLs, and that immunization of animals with these APCs led to the development of antigen-specific CTLs in vivo. Prior to administration to the subject, gene transfer and expression can be assayed using methods detailed below.

Isolation of Tumor Cells and Tumor Associated Antigens

The antigen can be a previously characterized antigen, e.g., gp100, MART or MUC-1, or it can be a yet unidentified antigen. Tumor cells that can be used for isolation of TAA, can be isolated by any method known in the art. In one embodiment, a biopsy sample is minced and a cell suspension created. Preferably, the tumor cells are separated from other cells (such as immune effector cells, e.g., T cells) using methods well known in the art.

The use of physical separation techniques include, but are not limited to, those based on differences in physical (density gradient centrifugation and counter-flow centrifugal elutriation), cell surface (lectin and antibody affinity), and vital staining properties (mitochondria-binding dye rho 123 and DNA-binding dye Hoechst 33342).

Monoclonal antibodies are another useful reagent for identifying markers associated with particular cell lineages and/or stages of differentiation can be used. The antibodies can be attached to a solid support to allow for crude separation. The separation techniques employed should maximize the retention of viability of the fraction to be collected. Various techniques of different efficacy can be employed to obtain "relatively crude" separations. Such separations are up to 10%, usually not more than about 5%, preferably not more than about 1%, of the total cells present not having the marker can remain with the cell population to be retained. The particular technique employed will depend upon efficiency of separation, associated cytotoxicity, ease and speed of performance, and necessity for sophisticated equipment and/or technical skill.

Identification of Antigen

Any conventional method, e.g., subtractive library, comparative Northern and/or Western blot analysis of normal and tumor cells, Serial Analysis Gene Expression or "SAGE" (U.S. Pat. No. 5,695,937) and SolidPHase Epitope REcovery ("SPHERE", described in PCT WO 97/35035) can be used to identify tumor antigens for use in the subject invention.

Another common strategy in the search for tumor antigens is to isolate tumor-specific T-cells and attempt to identify the antigens recognized by the T-cells. In patients with cancer, specific CTLs have been derived from lymphocytic infiltrates present at the tumor site. Weidmann, et al., supra. These TILs are unique cell population that can be traced back to sites of disease when they are labeled with indium and adoptively transferred. Alternatively, large libraries of putative antigens can be produced and tested. Using the "phage method" (Scott and Smith (1990) *Science* 249: 386–390; Cwirla, et al. (1990) *Proc. Natl. Acad. Sci.* 87:6387–6382; Devlin, et al. (1990) *Science* 249:404–406), very large libraries can be constructed. Another approach uses primarily chemical methods, of which the Geysen method (Geysen, et al. (1986) *Mol. Immunol.* 23:709–715; Geysen, et al. (1987) *J. Immunol. Method* 102:259–274) and the method of Fodor, et al. (1991) *Science* 251:767–773, are examples. Furka, et al. (1988) 14*th Inter. Cong. Bio.* Vol. 5, Abst. FR:013; Furka (1991) *Inter. J. Peptide Protein Res.* 37:487–493), Houghton (U.S. Pat. No. 4,683,211, issued December 1986) and Rutter, et al. (U.S. Pat. No. 5,010,175, issued Apr. 23, 1991) describe methods to produce a mixture of peptides that can be tested as agonists or antagonists.

SAGE analysis, noted above, can be employed to identify the antigens recognized by expanded immune effector cells such as CTLs. Briefly, SAGE analysis begins with providing complementary deoxyribonucleic acid (cDNA) from (1) the antigen-expressing population and (2) cells not expressing that antigen. Both cDNAs can be linked to primer sites. Sequence tags are then created, for example, using the appropriate primers to amplify the DNA. By measuring the differences in these tags between the two cell types, sequences which are aberrantly expressed in the antigen-expressing cell population can be identified.

In a further aspect of this invention, SolidPHase Epitope REcovery ("SPHERE", described in PCT WO 97/35035) can be used to identify tumor antigens. Briefly, SPHERE can be used to identify antigens by creating a library of molecules, preferably peptides, and attaching one type of molecule to a solid support via a releasable linker. At least a portion of the molecules bound to each support can be released and it can be determined if the antigen-specific immune effector cells recognized the peptide.

Thus, this invention also provides a screen to identify novel wild-type antigens that can be further modified and used to induce a cellular and a humoral immune response in the subject. The antigens gp100, MART or MUC-1, their biological activity in vitro and in vivo are positive controls.

Isolation, Culturing and Expansion of APCs, Including Dendritic Cells

The following is a brief description of two fundamental approaches for the isolation of APC. These approaches involve (1) isolating bone marrow precursor cells (CD34$^+$) from blood and stimulating them to differentiate into APC; or (2) collecting the precommitted APCs from peripheral blood. In the first approach, the patient must be treated with cytokines such as GM-CSF to boost the number of circulating CD34$^+$ stem cells in the peripheral blood.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal, PS et al. (1990) *PNAS* 87:7698–7702); Percoll gradient separations (Mehta-Damani, et al. (1994) *J. Immunol.* 153:996–1003); and fluorescence activated cell sorting techniques (Thomas, R. et al. (1993) *J. Immunol.* 151: 6840–52).

One technique for separating large numbers of cells from one another is known as countercurrent centrifugal elutriation (CCE). In this technique, cells are subject to simultaneous centrifugation and a washout stream of buffer which is constantly increasing in flow rate. The constantly increasing countercurrent flow of buffer leads to fractional cell separations that are largely based on cell size.

In one aspect of the invention, the APC are precommitted or mature dendritic cells which can be isolated from the white blood cell fraction of a mammal, such as a murine, simian or a human (See, e.g., WO 96/23060). The white blood cell fraction can be from the peripheral blood of the mammal. This method includes the following steps: (a) providing a white blood cell fraction obtained from a mammalian source by methods known in the art such as leukophoresis; (b) separating the white blood cell fraction of step (a) into four or more subfractions by countercurrent centrifugal elutriation, (c) stimulating conversion of monocytes in one or more fractions from step (b) to dendritic cells by contacting the cells with calcium ionophore or IL-4 and GM-CSF, (d) identifying the dendritic cell-enriched fraction from step (c), and (e) collecting the enriched fraction of step (d), preferably at about 4° C. One way to identify the dendritic cell-enriched fraction is by fluorescence-activated cell sorting. The white blood cell fraction can be treated with calcium ionophore in the presence of other cytokines, such as IL-12, GM-CSF or IL-4. The cells of the white blood cell fraction can be washed in buffer and suspended in Ca$^{++}$/Mg$^{++}$ free media prior to the separating step. The white blood cell fraction can be obtained by leukapheresis. The dendritic cells can be identified by the presence of at least one of the following markers: HLA-DR, HLA-DQ, or B7.2, and the simultaneous absence of the following markers: CD3, CD14, CD16,56,57, and CD 19, 20. Monoclonal antibodies specific to these cell surface markers are commercially available.

More specifically, the method requires collecting an enriched collection of white cells and platelets from leukapheresis that is then further fractionated by countercurrent centrifugal elutriation (CCE) (Abrahamsen T G et al. (1991) *J. Clin. Apheresis.* 6:48–53). Cell samples are placed in a special elutriation rotor. The rotor is then spun at a constant speed of, for example, 3000 rpm. Once the rotor has reached the desired speed, pressurized air is used to control the flow rate of cells. Cells in the elutriator are subjected to simultaneous centrifugation and a washout stream of buffer which is constantly increasing in flow rate. This results in fractional cell separations based largely but not exclusively on differences in cell size.

Large numbers of PBMCs (up to 1×10$^{10}$) can be obtained by leukapheresis and circulating immature DCs or hematopoietic progenitors can be subsequently isolated using several methods including but not limited to: metrizamide gradients (Freudenthal P. S. and Steinman, R. M. (1990) *Proc. Natl. Acad. Sci.* 87:7698–7702); Percoll gradients (Mehta-Damani, et al. (1994) *J. Immunol.* 153:996–1003); Nycodenz gradients (McLellan, et al. (1995) *J. Immunol. Methods* 184:81–89); elutriation of mononuclear cells of myeloid origin followed by removal of contaminating populations by flow cytometry using fluorescent antibodies directed against surface markers that are not expressed by DCs (e.g. CD14) and/or with magnetic beads coated with such antibodies (Czerniecki, et al. (1997)*J. Immunol.* 159: 3823–37).

In addition to direct isolation of immature DCs, peripheral blood monocytes can also serve as a pool of DC precursors. Monocytes can be =recovered from PBMC by elutriation, Ficoll and Percoll gradients or through their ability to adhere to plastic. Adherent layers of monocytes are typically cultured in GM-CSF+IL4 or GM-CSF+IL-13 to promote differentiation into immature DCs. Further purification of DCs obtained in this manner can be achieved by depletion of contaminating lymphocytes and monocytes/macrophages with specific antibodies plus complement or with antibody-coated magnetic beads (Sozzani, et al. (1997) *J. Immunol.* 9:271–96; Henderson, et al. (1997)*J. Immunol.* 159:635–43; Romani, et al. (1994) *J. Exp. Med.* 180:83–93).

Another approach to obtaining DCs from blood is positive selection of circulating $CD34^+$ hematopoietic progenitors using magnetic beads coated with CD34-specific antibodies (Siena, et al. (1995)*Exp. Hematol.* 23:1463–71). To improve yield, the frequency of circulating progenitor cells can be increased by treating the host with various combinations of cytokines such as Flt-3 ligand (Sudo, et al. (1997) *Blood* 89:3186–91), IL-3, G-CSF (Siena, et al. (1995)) and GM-CSF (Siena, et al. (1989) *Blood* 74:1905- ). Treatment of cancer patients with cyclophosphamide also leads to mobilization of $CD34^+$ stem cells into peripheral blood (Siena, et al. (1989)).

A basic approach to deriving DCs from bone marrow consists of bone marrow collection followed by depletion of all non-DC cell types (lymphocytes, granulocytes, monocytes/macrophages) for example with a cocktail of specific antibodies and complement (Inaba, et al. (1992)*J. Exp. Med.* 176:1693–1702). The remaining cells are then cultured in GM-CSF+IL-4 to promote the growth and differentiation of DCs. Alternatively, $CD34^+$ precursor stem cells can be positively selected from bone marrow.

$CD34^+$ precursor stem cells isolated from blood or bone marrow can be differentiated into DCs by culture in various combinations of cytokines such as GM-CSF, SCF (stem cell factor), TNF-α and Flt-3 ligand (Siena, et al. (1995); Maraskovsky, et al. (1995) *Blood* 86:420a).

There is no known cell surface marker expressed by DCs exclusively and, therefore, DCs are typically identified by their veiled morphology and by the presence of a set of characteristic surface markers (MHC Class I, MHC Class II, B7.1, B7.2, CD13, CD33, CD40, etc.) and the absence of surface markers typical of macrophages (CD 14) or lymphocytes (CD3, CD4, CD8).

Immature DCs isolated directly from blood or derived from blood monocytes or bone marrow can effectively take up and process antigen for presentation to T lymphocytes. However, further maturation is required for the DCs to acquire the ability to effectively prime antigen-specific T cells (Steinman, R. M. (1991) *Annu. Rev. Immunol.* 9:271–96). This maturation process is believed to occur in vivo after antigen uptake and exposure to inflammatory agents and can be reproduced in vitro by exposure of the DCs to stimuli such as TNF-α, lipopolysaccharide (LPS), CD40 ligand, IL-1β or calcium ionophores (Cella, et al. (1997) *Nature* 388:782–87; Henderson, et al. (1997); Czerniecki, et al. (1997)). For our purpose, transduced or peptide-pulsed immature DCs could be used directly for immunization with the maturation process occurring in vivo or, alternatively, antigen-presenting DCs could be further matured in vitro prior to administration as desired.

Alternatively, muteins of the antigen as well as allogeneic and antigens from a different species, of previously characterized antigens are useful in the subject invention. MART1 and gp100 are melanocyte differentiation antigens specifically recognized by HLA-A2 restricted tumor-infiltrating lymphocytes (TILs) derived from patients with melanoma, and appear to be involved in tumor regression (Kawakami, Y., et al. (1994) *Proc. Natl. Acad. Sci. USA* 91:6458–62; Kawakami, Y., et al. (1994) *Proc. Natl. Acad. Sci. USA* 91:91:3515–9). Recently, the mouse homologue of human MART-1 has been isolated. The full-length open reading frame of the mouse MART1 consists of 342 bp, encoding a protein of 113 amino acid residues with a predicted molecular weight of 13 kDa. Alignment of human and murine MART1 amino acid sequences showed 68.6% identity.

The murine homologue of gp100 has also been identified. The open reading frame consists of 1,878 bp, predicting a protein of 626 amino acid residues which exhibits 75.5% identity to human gp100.

In vitro confirmation of the immunogenicity of an putative antigen of this invention can be confirmed using the method described below which assays for the production of CTLs.

Vectors Useful in Genetic Modifications

In general, genetic modifications of cells employed in the present invention are accomplished by introducing a vector containing a polypeptide or cDNA encoding an antigen. A variety of different gene transfer vectors, including viral as well as non-viral systems can be used. Viral vectors useful in the genetic modifications of this invention include, but are not limited to adenovirus, adeno-associated virus vectors, retroviral vectors and adeno-retroviral chimeric vectors.

Construction of Recombinant Adenoviral Vectors or Adeno-Associated Virus Vectors Adenovirus and adeno-associated virus vectors useful in the genetic modifications of this invention may be produced according to methods already taught in the art. (see, e.g., Karlsson, et al. (1986)*EMBO* 5:2377; Carter (1992) *Current Opinion in Biotechnology* 3:533–539; Muzcyzka (1992) *Current Top. Microbiol. Immunol.* 158:97–129; GENE TARGETING: A PRACTICAL APPROACH (1992) ed. A. L. Joyner, Oxford University Press, NY). Several different approaches are feasible. Preferred is the helper-independent replication deficient human adenovirus system.

The recombinant adenoviral vectors based on the human adenovirus 5 (*Virology* 163:614–617, 1988) are missing essential early genes from the adenoviral genome (usually E1A/E1B), and are therefore unable to replicate unless grown in permissive cell lines that provide the missing gene products in trans. In place of the missing adenoviral genomic sequences, a transgene of interest can be cloned and expressed in cells infected with the replication deficient adenovirus. Although adenovirus-based gene transfer does not result in integration of the transgene into the host genome (less than 0.1% adenovirus-mediated transfections result in transgene incorporation into host DNA), and therefore is not stable, adenoviral vectors can be propagated in high titer and transfect non-replicating cells. Human 293 cells, which are human embryonic kidney cells transformed with adenovirus E1A/E1B genes, typify useful permissive cell lines and are commercially available from the ATCC. However, other cell lines which allow replication-deficient adenoviral vectors to propagate therein can be used, including HeLa cells.

Additional references describing adenovirus vectors and other viral vectors which could be used in the methods of the present invention include the following: Horwitz, M. S., Adenoviridae and Their Replication, in Fields, B., et al. (eds.) VIROLOGY, Vol. 2, Raven Press New York, pp. 1679–1721, 1990); Graham, F., et al., pp. 109–128 in METHODS IN MOLECULAR BIOLOGY, Vol. 7: GENE TRANSFER AND EXPRESSION PROTOCOLS, Murray, E. (ed.), Humana Press, Clifton, N.J. (1991); Miller, N., et al. (1995) *FASEB Journal* 9:190–199 Schreier, H (1994) *Pharmaceutica Acta Helvetiae* 68:145–159; Schneider and French (1993) *Circulation* 88:1937–1942; Curiel D. T., et al. (1992) *Human Gene Therapy* 3: 147–154; Graham, F. L., et al., WO 95/00655 (5 Jan. 1995); Falck-Pedersen, E. S., WO 95/16772 (22 Jun. 1995); Denefle, P., et al., WO 95/23867 (8 Sep. 1995); Haddada, H., et al., WO 94/26914 (24 Nov. 1994); Perricaudet, M., et al., WO 95/02697 (26 Jan. 1995); Zhang, W., et al., WO 95/25071 (12 Oct. 1995). A variety of adenovirus plasmids are also available from commercial sources, including, e.g., Microbix Biosystems of Toronto, Ontario (see, e.g., Microbix Product Information Sheet: Plasmids for Adenovirus Vector Construction, 1996). See also, the papers by Vile, et al. (1997) *Nature Biotechnology* 15: 840–841; Feng, et al. (1997) *Nature Biotechnology,* 15: 866–870, describing the construction and use of adeno-retroviral chimeric vectors that can be employed for genetic modifications.

Additional references describing AAV vectors which could be used in the methods of the present invention include the following: Carter, B., HANDBOOK OF PARVOVIRUSES, Vol. I, pp. 169–228, 1990; Berns, VIROLOGY, pp. 1743–1764 (Raven Press 1990); Carter, B. (1992) *Curr. Opin. Biotechnol.* 3:533–539; Muzyczka, N. (1992) *Current Topics in Micro and Immunol,* 158: 92–129; Flotte, T. R., et al. (1992) *Am. J. Respir. Cell Mol. Biol.* 7:349–356; Chatterjee, et al. (1995) *Ann. NY Acad. Sci.* 770: 79–90; Flotte, T. R., et al., WO 95/13365 (18 May 1995); Trempe, J. P., et al., WO 95/13392 (18 May 1995); Kotin, R., Human Gene Therapy, 5: 793–801, 1994; Flotte, T. R., et al. (1995) *Gene Therapy* 2:357–362; Allen, J. M., WO 96/17947 (13 Jun. 1996); and Du, et al. (1996) *Gene Therapy* 3: 254–261.

Construction of Retroviral Vectors

Although adenoviral vectors are preferred, it is possible to use retroviral vectors, which are produced recombinantly by procedures already taught in the art. For example, WO 94/29438 describes the construction of retroviral packaging plasmids and packaging cell lines. As is apparent to the skilled artisan, the retroviral vectors useful in the methods of this invention are capable of infecting the cells described herein. The techniques used to construct vectors, and transfix and infect cells are widely practiced in the art. Examples of retroviral vectors are those derived from murine, avian or primate retroviruses. Retroviral vectors based on the Moloney murine leukemia virus (MoMLV) are the most commonly used because of the availability of retroviral variants that efficiently infect human cells. Other suitable vectors include those based on the Gibbon Ape Leukemia Virus (GALV) or HIV.

In producing retroviral vector constructs derived from the Moloney murine leukemia virus (MoMLV), in most cases, the viral gag, pol and env sequences are removed from the virus, creating room for insertion of foreign DNA sequences. Genes encoded by the foreign DNA are usually expressed under the control of the strong viral promoter in the LTR. Such a construct can be packed into viral particles efficiently if the gag, pol and env functions are provided in trans by a packaging cell line. Thus, when the vector construct is introduced into the packaging cell, the gag-pol and env proteins produced by the cell, assemble with the vector RNA to produce infectious virions that are secreted into the culture medium. The virus thus produced can infect and integrate into the DNA of the target cell, but does not produce infectious viral particles since it is lacking essential packaging sequences. Most of the packaging cell lines currently in use have been transfected with separate plasmids, each containing one of the necessary coding sequences, so that multiple recombination events are necessary before a replication competent virus can be produced. Alternatively, the packaging cell line harbors an integrated provirus. The provirus has been crippled so that, although it produces all the proteins required to assemble infectious viruses, its own RNA cannot be packaged into virus. Instead, RNA produced from the recombinant virus is packaged. The virus stock released from the packaging cells thus contains only recombinant virus.

The range of host cells that may be infected by a retrovirus or retroviral vector is determined by the viral envelope protein. The recombinant virus can be used to infect virtually any other cell type recognized by the env protein provided by the packaging cell, resulting in the integration of the viral genome in the transduced cell and the stable production of the foreign gene product. In general, murine ecotropic env of MoMLV allows infection of rodent cells, whereas amphotropic env allows infection of rodent, avian and some primate cells, including human cells. Amphotropic packaging cell lines for use with MoMLV systems are known in the art and commercially available and include, but are not limited to, PA12 and PA317. Miller, et al. (1985) *Mol. Cell. Biol.* 5:431–437; Miller, et al. (1986) *Mol. Cell. Biol.* 6:2895–2902; and Danos, et al. (1988) *Proc. Natl. Acad. Sci. USA* 85:6460–6464. Xenotropic vector systems exist which also allow infection of human cells.

The host range of retroviral vectors has been altered by substituting the env protein of the base virus with that of a second virus. The resulting, "pseudotyped", virus has the host range of the virus donating the envelope protein and expressed by the packaging cell line. Recently, the G-glycoprotein from vesicular stomatitis virus (VSV-G) has been substituted for the MoMLV env protein. Burns, et al. (1993) *Proc. Natl. Acad. Sci USA* 90:8033–8037; and PCT patent application WO 92/14829. Since infection is not dependent on a specific receptor, VSV-G pseudotyped vectors have a broad host range.

A marker gene can be included in the vector for the purpose of monitoring successful transduction and for selection of cells into which the DNA has been integrated, as against cells which have not integrated the DNA construct. Various marker genes include, but are not limited to, antibiotic resistance markers, such as resistance to G418 or hygromycin. Less conveniently, negative selection may be used, including, but not limited to, where the marker is the HSV-tk gene, which will make the cells sensitive to agents such as acyclovir and gancyclovir. Alternatively, selections could be accomplished by employment of a stable cell surface marker to select for transgene expressing cells by FACS sorting. The NeoR (neomycin/G418 resistance) gene is commonly used but any convenient marker gene whose sequences are not already present in the recipient cell, can be used.

The viral vector can be modified to incorporate chimeric envelope proteins or nonviral membrane proteins into retroviral particles to improve particle stability and expand the host range or to permit cell type-specific targeting during infection. The production of retroviral vectors that have altered host range is taught, for example, in WO 92/14829 and WO 93/14188. Retroviral vectors that can target specific cell types in vivo are also taught, for example, in Kasahara, et al. (1994) *Science* 266:1373–1376. Kasahara, et al. describe the construction of a Moloney leukemia virus (MoMLV) having a chimeric envelope protein consisting of human erythropoietin (EPO) fused with the viral envelope protein. This hybrid virus shows tissue tropism for human red blood progenitor cells that bear the receptor for EPO, and is therefore useful in gene therapy of sickle cell anemia and thalassemia. Retroviral vectors capable of specifically targeting infection of cells are preferred for in vivo gene therapy.

The viral constructs can be prepared in a variety of conventional ways. Numerous vectors are now available which provide the desired features, such as long terminal repeats, marker genes, and restriction sites, which may be further modified by techniques known in the art. The constructs may encode a signal peptide sequence to ensure that cell surface or secreted proteins encoded by genes are properly processed post-translationally and expressed on the cell surface if appropriate. Preferably, the foreign gene(s) is under the control of a cell specific promoter.

Expression of the transferred gene can be controlled in a variety of ways depending on the purpose of gene transfer and the desired effect. Thus, the introduced gene may be put under the control of a promoter that will cause the gene to be expressed constitutively, only under specific physiologic conditions, or in particular cell types.

The retroviral LTR (long terminal repeat) is active in most hematopoietic cells in vivo and will generally be relied upon for transcription of the inserted sequences and their constitutive expression (Ohashi, et al. (1992) *Proc. Natl. Acad. Sci.* 89:11332; Correll, et al. (1992) *Blood* 80:331). Other suitable promoters include the human cytomegalovirus (CMV) immediate early promoter and the U3 region promoter of the Moloney Murine Sarcoma Virus (MMSV), Rous Sarcoma Virus (RSV) or Spleen Focus Forming Virus (SFFV).

Examples of promoters that may be used to cause expression of the introduced sequence in specific cell types include Granzyme A for expression in T-cells and NK cells, the CD34 promoter for expression in stem and progenitor cells, the CD8 promoter for expression in cytotoxic T-cells, and the CD11b promoter for expression in myeloid cells.

Inducible promoters may be used for gene expression under certain physiologic conditions. For example, an electrophile response element may be used to induce expression of a chemoresistance gene in response to electrophilic molecules. The therapeutic benefit may be further increased by targeting the gene product to the appropriate cellular location, for example the nucleus, by attaching the appropriate localizing sequences.

The vector construct is introduced into a packaging cell line which will generate infectious virions. Packaging cell lines capable of generating high titers of replication-defective recombinant viruses are known in the art, see for example, WO 94/29438. Viral particles are harvested from the cell supernatant and purified for in vivo infection using methods known in the art such as by filtration of supernatants 48 hours post transfection. The viral titer is determined by infection of a constant number of appropriate cells (depending on the retrovirus) with titrations of viral supernatants. The transduction efficiency can be assayed 48 hours later by a variety of methods, including Southern blotting.

Non-viral vectors, such as plasmid vectors useful in the genetic modifications of this invention, can be produced according to methods taught in the art. References describing the construction of non-viral vectors include the following: Ledley, F D, *Human Gene Therapy* 6: 1129–1144, 1995; Miller, N., et al., FASEB Journal 9: 190–199, 1995; Chonn, A., et al., *Curr. Opin. in Biotech.* 6: 698–708, 1995; Schofield, J P, et al., (1995) *British Med. Bull.* 51: 56–71, Brigham, K. L., et al., (1993) *J. Liposome Res.* 3: 31–49, Brigham, K. L., WO 91/06309 (16 May 1991); Felgner, P. L., et al., WO 91/17424 (14 Nov. 1991); Solodin, et al., (1995) Biochemistry 34: 13537–13544, WO 93/19768 (14 Oct. 1993); Debs, et al., WO 93/25673; Felgner, P. L., et al., U.S. Pat. No. 5,264,618 (Nov. 23, 1993); Epand, R. M., et al., U.S. Pat. No. 5,283,185 (Feb. 1, 1994); Gebeyehu, et al., U.S. Pat. No. 5,334,761 (Aug. 2, 1994); Felgner, P. L., et al., U.S. Pat. No. 5,459,127 (Oct. 17, 1995); Overell, R. W., et al., WO 95/28494 (26 Oct. 1995); Jessee, WO 95/02698 (26 Jan. 1995); Haces and Ciccarone, WO 95/17373 (29 Jun. 1995); Lin, et al., WO 96/01840 (25 Jan. 1996).

Assessing Efficacy of Gene Transfer

The efficacy of gene transfer into the cells of the subject can be monitored by any method known in the art. For example, as described above, a reporter or marker gene can be included in the gene delivery vehicle to facilitate identification of those cells into which the vehicle is successfully incorporated. Especially in the in vitro and ex vivo contexts, marker genes may prove especially helpful. Screening markers or reporter genes are genes that encode a product that can readily be assayed. Non-limiting examples of screening markers include genes encoding for green fluorescent protein (GFP) or genes encoding for a modified fluorescent protein.

Preferably, the marker gene included in the delivery vehicle is a selectable marker. A "positive" selectable marker gene encodes a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Negative selectable marker genes encode a product that allows cells expressing that product to be selectively killed. For example, as described above the conditionally activated cytotoxic agent may also be a selectable marker such as HSV-tk. Cells expressing this gene can be selectively killed using gancyclovir or acyclovir.

Presentation of Antigen by the APC

Peptide fragments from antigens must first be bound to peptide binding receptors (major histocompatibility complex class I and class II molecules) that display the antigenic peptides on the surface of the APCs. Palmer E. and Cresswell (1998) *Annu. Rev. Immunol.* 16:323 and Germain R. N. (1996) *Immunol. Rev.* 151:5. T lymphocytes produce an antigen receptor that they use to monitor the surface of APCs for the presence of foreign peptides. The antigen receptors on $CD4^+$ T cells recognize antigenic peptides bound to MHC class II molecules whereas the receptors on $CD8^+$ T cells react with antigens displayed on class I molecules. For a general review of the methods for presentation of exogeneous antigen by APC, see Raychaudhuri and Rock (1998) Nature Biotechnology 16:1025.

For purposes of immunization, antigens can be delivered to antigen-presenting cells as protein/peptide or in the form of polynucleotides encoding the protein/peptide ex vivo or in vivo. The methods described below focus primarily on DCs which are the most potent, preferred APCs.

Several different techniques have been described to produce genetically modified APCs. These include: (1) the introduction into the APCs of polynucleotides that express antigen or fragments thereof; (2) infection of APCs with recombinant vectors to induce endogenous expression of antigen; and (3) introduction of tumor antigen into the DC cytosol using liposomes. (See, Boczkowski D. et al. (1996) *J. Exp. Med.* 184:465; Rouse et al. (1994) *J. Virol.* 68:5685; and Nair et al. (1992) *J. Exp. Med.* 175:609). For the purpose of this invention, any method which allows for the introduction and expression of the heterologous or non-self antigen and presentation by the MHC on the surface of the APC is within the scope of this invention.

Several techniques have been described for the presentation of exogenous protein and/or peptide by the APC. These techniques are briefly described below.

Antigen Pulsing

Pulsing is accomplished in vitro/ex vivo by exposing APCs to antigenic protein or peptide(s). The protein or peptide(s) are added to APCs at a concentration of 1–10 $\mu$m for approximately 3 hours. Paglia et al. (1996) J. Exp. Med. 183:317, has shown that APC incubated with whole protein in vitro were recognized by MHC class I-restricted CTLs, and that immunization of animals with these APCs led to the development of antigen-specific CTLs in vivo.

Protein/peptide antigen can also be delivered to APC in vivo and presented by the APC. Antigen is preferably delivered with adjuvant via the intravenous, subcutaneous, intranasal, intramuscular or intraperitoneal route of delivery. Grant E. P. and Rock K. L. (1992) *J. Immunol.* 148:13; Norbury, C. C. et al. (1995) *Immunity* 3:783; and Reise-Sousa C. and Germain R. N. (1995) *J. Exp. Med.* 182:841.

Antigen Painting

Another method which can be used is termed "painting". It has been demonstrated that glycosyl-phosphotidylinositol (GPI)-modified proteins possess the ability to reincorporate themselves back into cell membranes after purification. Hirose et al. (1995) *Methods Enzymol.* 250:582; Medof et al. (1984) *J. Exp. Med.* 160:1558; Medof (1996) *FASEB J.* 10:574; and Huang et al. (1994) *Immunity* 1:607, have exploited this property in order to create APCs of specific composition for the presentation of antigen to CTLs. Expression vectors for $\beta$2-microglobulin and the HLA-A2.1 allele were first devised. The proteins were expressed in Schneider S2 *Drosophila melanogaster* cells, known to support GPI-modification. After purification, the proteins could be incubated together with a purified antigenic peptide which resulted in a trimolecular complex capable of efficiently inserting itself into the membranes of autologous cells. In essence, these protein mixtures were used to "paint" the APC surface, conferring the ability to stimulate a CTL clone that was specific for the antigenic peptide. Cell coating was shown to occur rapidly and to be protein concentration dependent. This method of generating APCs bypasses the need for gene transfer into the APC and permits control of antigenic peptide densities at the cell surfaces.

Foster Antigen Presenting Cells

Foster APCs are derived from the human cell line 174xCEM.T2, referred to as T2, which contains a mutation in its antigen processing pathway that restricts the association of endogenous peptides with cell surface MHC class I molecules (Zweerink et al. (1993) *J. Immunol.* 150:1763). This is due to a large homozygous deletion in the MHC class II region encompassing the genes TAP1, TAP2, LMP1, and LMP2, which are required for antigen presentation to MHC class 1-restricted CD8+ CTLs. In effect, only "empty" MHC class I molecules are presented on the surface of these cells. Exogenous peptide added to the culture medium binds to these MHC molecules provided that the peptide contains the allele-specific binding motif. These T2 cells are referred to herein as "foster" APCs. They can be used in conjunction with this invention to present the heterologous, altered or control antigen.

Transduction of T2 cells with specific recombinant MHC alleles allows for redirection of the MHC restriction profile. Libraries tailored to the recombinant allele will be preferentially presented by them because the anchor residues will prevent efficient binding to the endogenous allele.

High level expression of MHC molecules makes the APC more visible to the CTLs. Expressing the MHC allele of interest in T2 cells using a powerful transcriptional promoter (e.g., the CMV promoter) results in a more reactive APC (most likely due to a higher concentration of reactive MHC-peptide complexes on the cell surface).

Viral Vectors

DCs can be transduced with viral vectors encoding a relevant TAA. Viral vectors that can be used include recombinant poxviruses such as vaccinia and fowlpox virus (Bronte, et al. (1997) *Proc. Natl. Acad. Sci.* 94:3183–88; Kim, et al. (1997) *J. Immunother.* 20:276–86) and, preferentially, adenovirus (Arthur, et al. (1997) *Cancer Gene Ther.* 4:17–25; Wan, et al. (1997) *Hum. Gene Ther.* 8:1355–63; our own results). It is conceivable that alternative virus vectors (e.g. retrovirus) may also prove suitable for transduction of human DCs (Marin, et al. (1996). *J. Virol.* 70:2957–62).

In vitro/ex vivo, exposure of human DCs to adenovirus (Ad) vector at a multiplicity of infection (MOI) of 500 for 16–24 h in a minimal volume of serum-free medium reliably gives rise to transgene expression in 90–100% of DCs. The efficiency of transduction can be assessed by immunofluorescence using fluorescent antibodies specific for the tumor antigen being expressed (Kim, et al. (1997)). Alternatively, the antibodies can be conjugated to an enzyme (e.g. HRP) giving rise to a colored product upon reaction with the substrate. The actual amount of TAA being expressed by the DCs can be evaluated by ELISA.

In vivo transduction of DCs can potentially be accomplished by administration of Ad vector via different routes including intravenous, intramuscular, intranasal, intraperitoneal or cutaneous delivery. The preferred route of administration is cutaneous delivery at multiple sites using a total dose of approximately $1\times10^{10}$–$1\times10^{12}$ i.u. Levels of in vivo transduction can be roughly assessed by co-staining with antibodies directed against DC marker(s) and the TAA being expressed. The staining procedure can be carried out on biopsy samples from the site of administration or on cells from draining lymph nodes or other organs where DCs may have migrated (Condon, et al. (1996) *Nature Med.* 2:1122–28; Wan, et al. (1997) *Human Gene Therapy* 8:1355–1363). The amount of TAA being expressed at the site of injection or in other organs where transduced DCs may have migrated can be evaluated by ELISA on tissue homogenates.

Non-Viral Vectors

Although viral gene delivery is more efficient, dendritic cells can also be transduced in vitro/ex vivo by non-viral gene delivery methods such as electroporation, calcium phosphate precipitation or cationic lipid/plasmid DNA complexes (Arthur, et al. (1997) *Cancer Gene Therapy* 4:17–25). In vivo transduction of dendritic cells can potentially be accomplished by administration of cationic lipid/plasmid DNA complexes delivered via the intravenous, intramuscular, intranasal, intraperitoneal or cutaneous route of administration. Gene gun delivery or injection of naked plasmid DNA into the skin also leads to transduction of DCs (Condon, et al. (1996), supra; Raz, et al. (1994) *Proc. Natl. Acad. Sci.* 91:9519–23).

The transduction efficiency and levels of transgene expression can be assessed as described above for viral vectors.

Compositions and Methods for Therapeutic Application

In the context of cancer gene therapy, the invention consists of amplifying the host immune response against tumor by co-administering allogeneic and autologous DCs expressing TAA(s). Autologous DCs provide cognate presentation of a tumor antigen to MHC-compatible T lymphocytes while allogeneic DCs are used to stimulate high frequency alloreactive T lymphocytes and thereby induce local production of stimulatory cytokines that will support and amplify the specific host immune response against tumor.

Reagents

Autologous DCs are derived as described above. The preferred method is isolation of monocytes from peripheral blood followed by in vitro differentiation into immature DCs. Immature autologous DCs are transduced with a vector, preferably adenovirus, expressing a relevant TAA(s). Allogeneic DCs are derived from a different individual in the same manner or, alternatively, a dendritic cell line as opposed to primary cells could be used as a source of allogeneic DCs. As mentioned above, the allogeneic DCs may or may not have to be transduced as well.

Allogeneic DCs (or DC line) should be pre-tested and selected for their ability to induce a strong allogeneic reaction on the part of the intended recipient. This can be accomplished by HLA-typing (select allogeneic DCs with the most mismatched HLA alleles) or in a functional mixed lymphocyte reaction (MLR). In an MLR, lymphocytes or purified T lymphocytes from the patient to be treated are stimulated with inactivated (irradiated or mitomycin C-treated) allogeneic DCs and the proliferative response induced is measured by tritiated thymidine incorporation after 5–6 days of culture. Allogeneic DCs that elicit the highest levels of proliferation are selected for co-administration with transduced autologous DCs.

EXAMPLE 1

Ex Vivo Transduction of Autologous DCS

Autologous DCs are transduced ex vivo, preferably with an Ad vector encoding a TAA (500 MOI for 24 h). At this point, the DCs can be administered or can be further matured by exposure to TNF-α prior to administration. The former option is preferred. At the time of administration, transduced autologous DCs are mixed with allogeneic primary DCs or an allogeneic DC line and the mixture is delivered i.v. or s.c. It is estimated that doses of autologous and allogeneic DCs can range from approximately $5 \times 10^7 - 5 \times 10^9$ each with up to 6 doses being delivered at intervals of approximately 3–6 weeks.

EXAMPLE 2

Ex Vivo Pulsing of Autologous DCS

In this instance, the protocol is the same as described in example 1, except that instead of being transduced, autologous DCs are pulsed with protein or peptide epitopes from a given TAA(s) (1–10 μm protein/peptide for approximately 3 h).

EXAMPLE 3

In Vivo Transduction of Autologous DCS

Autologous DCs are transduced in vivo, preferably by cutaneous administration of a TAA-encoding Ad vector at multiple sites (total dose of $1 \times 10^{10} - 1 \times 10^{12}$ i.u.). The allogeneic primary DCS or DC line are either mixed with the virus and administered concurrently or are administered separately, immediately after virus, at the same sites. The former option is preferred. It is estimated that the dose of allogeneic DCs can range from approximately $5 \times 10^7 - 5 \times 10^9$ and that treatment can be repeated up to six times at intervals of approximately 3–6 weeks.

In Vitro Assay to Determine Efficacy—Animal Model

In Vitro Assay

As described above, the relative potency of different preparations of allogeneic DCs to stimulate lymphocytes from the patient to be treated can be evaluated in vitro using the well-described mixed lymphocyte reaction (MLR). In addition, the relative ability of transduced autologous DCs±allogeneic DCs to elicit cytolytic effector cells capable of lysing tumor cells can also be tested in vitro. For this purpose, transduced autologous DCs expressing a relevant TAA±allogeneic DCs are used to stimulate autologous lymphocytes (or purified CD8+ T cells) and, after several rounds of stimulation, the effector cells generated are tested for their ability to recognize tumor or other target cells expressing the TAA of interest. Various culture conditions have been described that will support the generation of effector cells (Kim, et al. (1997) Supra,; Mehta-Damani, et al. (1994) Supra,; Tsai, et al. (1997) *J. Immunol.* 158:1796–1802; Bakker, et al. (1995) *Cancer Research* 55:5330–34). The development of TAA-specific effector cells can be measured by several methods including cytokine production (e.g. TNF-α, interferon-γ) upon recognition of TAA-expressing targets or lysis of TAA-expressing target cells as assessed by release of various intracellular labels/markers such as $^{51}$Chromium or lactose dehydrogenase (LDH).

Animal Model

Figure 3A:
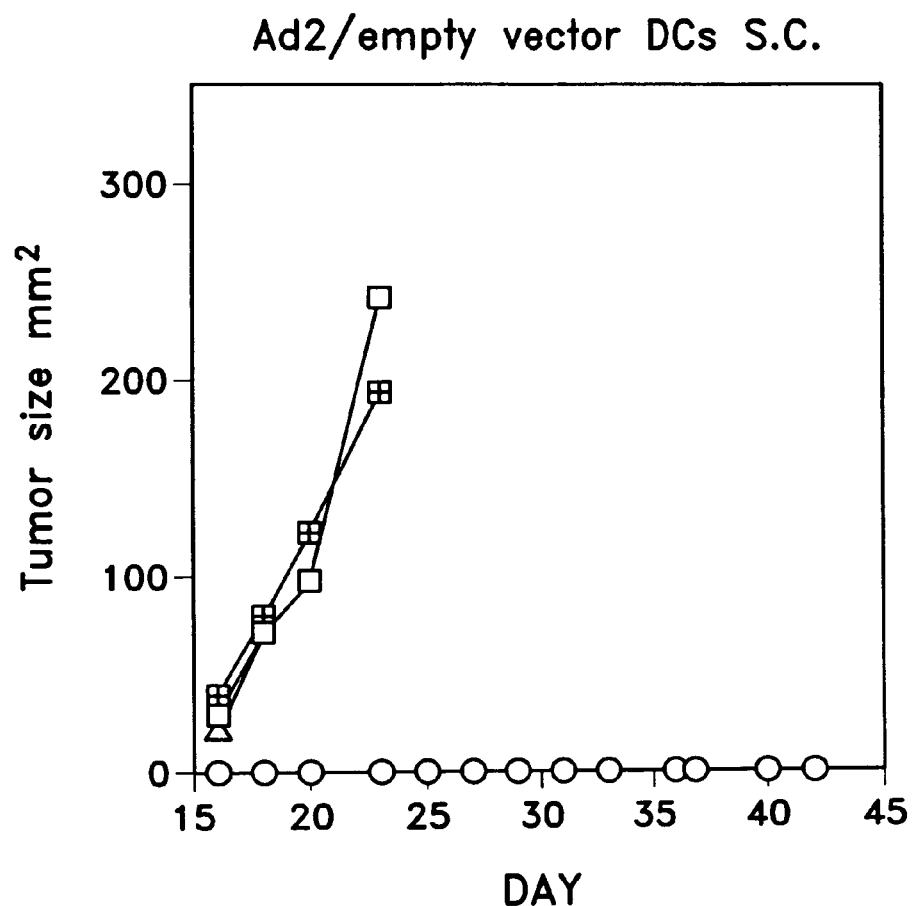
FIG. 3 shows the results of an experiment with B16 melanoma active treatment model. Groups of 5 C57BL/6 mice received a subcutaneous injection of $1.5 \times 10^5$ B16 melanoma cells and were treated 4 days later with a subcutaneous administration of $5 \times 10^5$ bone marrow-derived dendritic cells (DCs) transfected with adenovirus vector encoding human gp100 (Ad2/hugp 100 DCs) or mouse TRP-2 (Ad2/mTRP-2 DCs). DCs infected with an adenovirus vector lacking a transgene served as a negative control (Ad2/empty vector DCs). Tumor growth was monitored over time. The results indicate that inhibition of tumor growth through active immunization against tumor antigen is feasible but more difficult to achieve than pre-immunization against tumor.
Figure 3B:
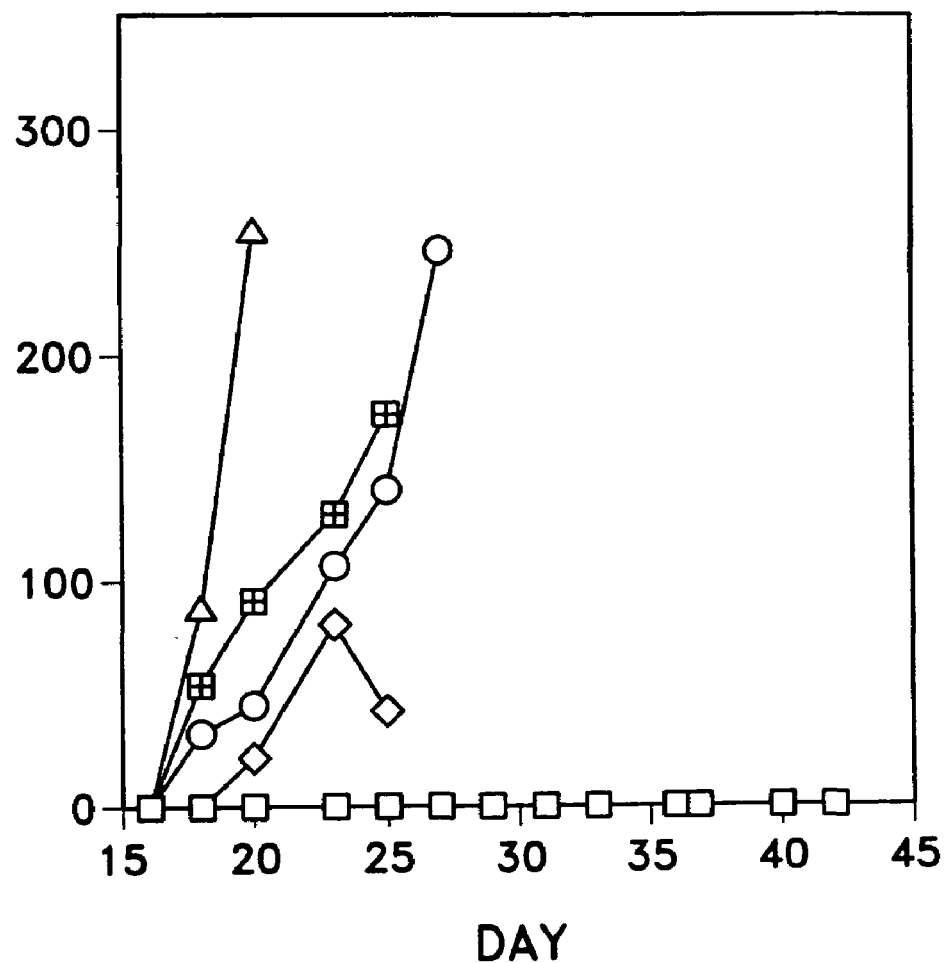
Figure 3C:
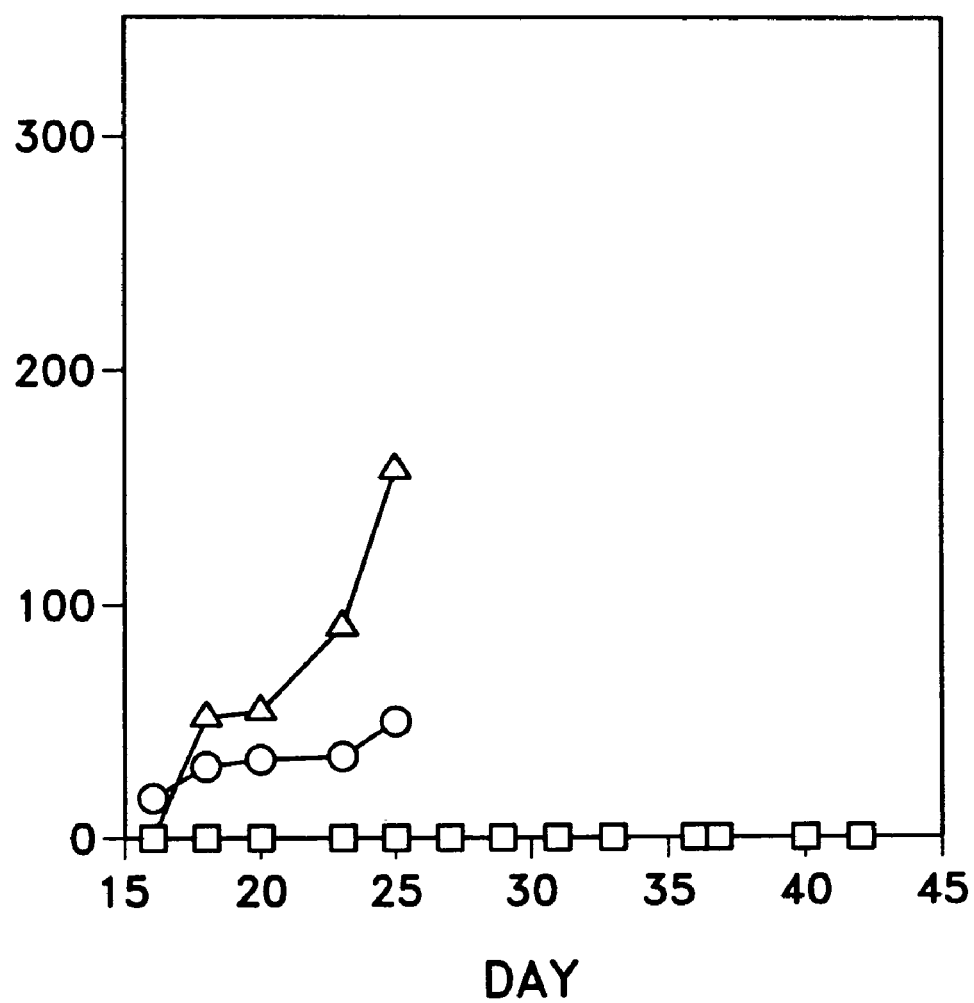

The efficacy of the planned strategy is best assessed in an animal model. The murine B16 melanoma model is one model. In this model, B16 melanoma cells are injected into syngeneic C57BL/6 mice either s.c. or i.v. to give rise to a local subcutaneous tumor or produce lung metastases, respectively. The relative immunizing potential of transduced autologous DCs±allogeneic DCs can be tested in a pre-immunization or active treatment setting. FIG. 3 shows the results of one experiment using this model.

Figure 2A:
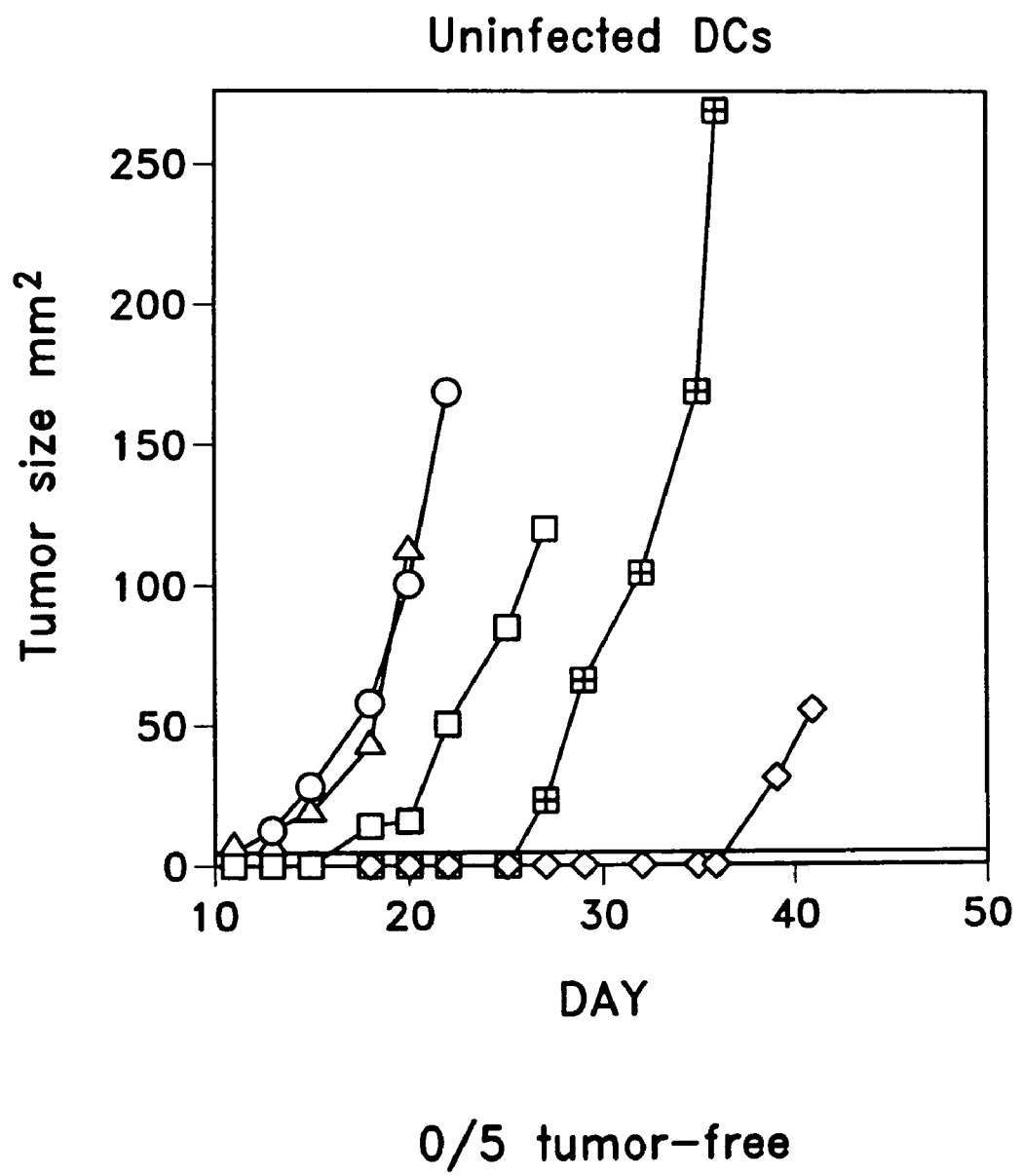
FIG. 2 shows the results of B16 melamona immunization model. Groups of 5 C57BL/6 mice were immunized against the gp100 or TRP-2 melanoma antigen by intraveneous injection of $5 \times 10^5$ bone marrow-derived dendritic cells (DCs) transfected with adenovirus vector encoding human gp100 (Ad2/hugp100 DCs) or mouse TRP-2 (Ad2/mTRP-2 DCs). Uninfected DCs serve as a negative control. Two weeks after immunization, the mice were challenged with a subcutaneous injection of $2 \times 10^4$ B16 melanoma cells and tumor growth was monitored over time. The results indicate that pre-immunization against tumor antigen is effective in inducing anti-tumor immunity.
Figure 2B:
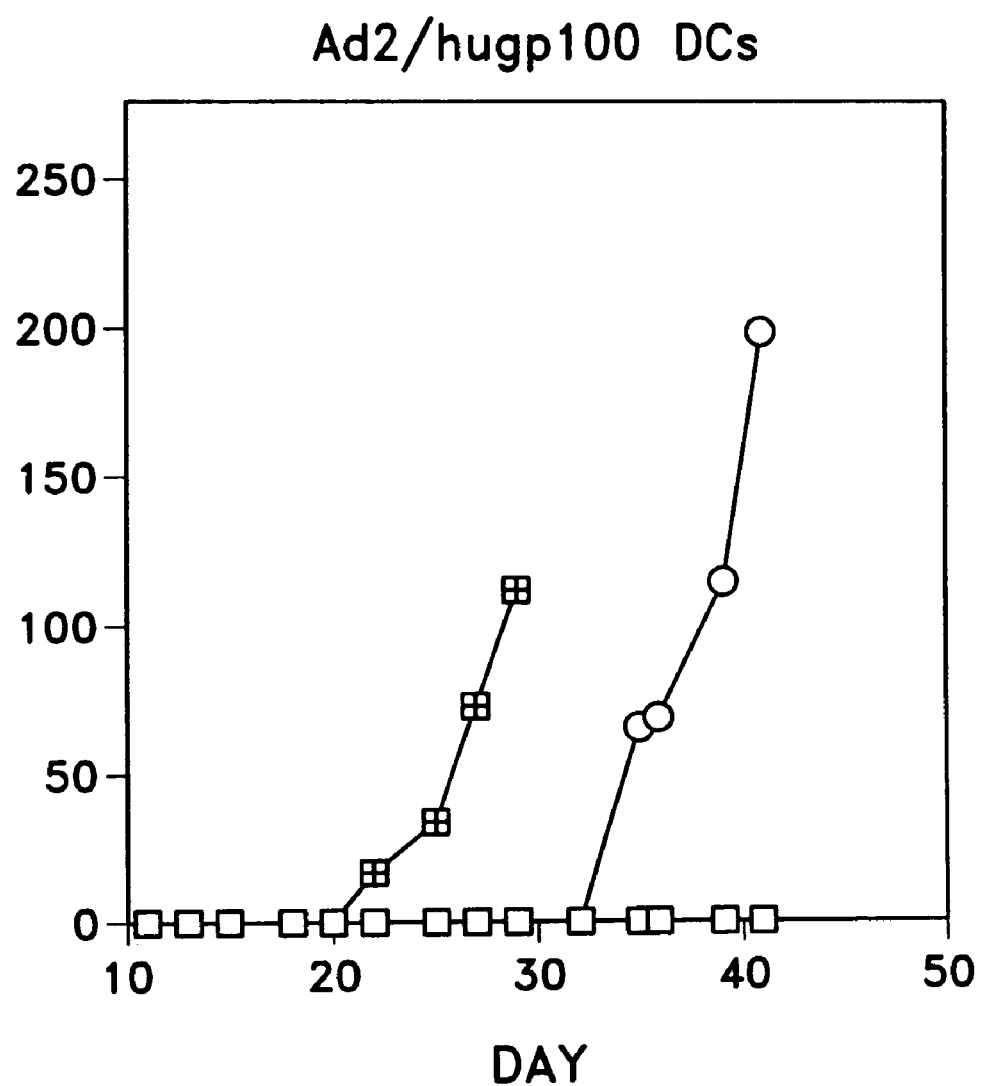
Figure 2C:
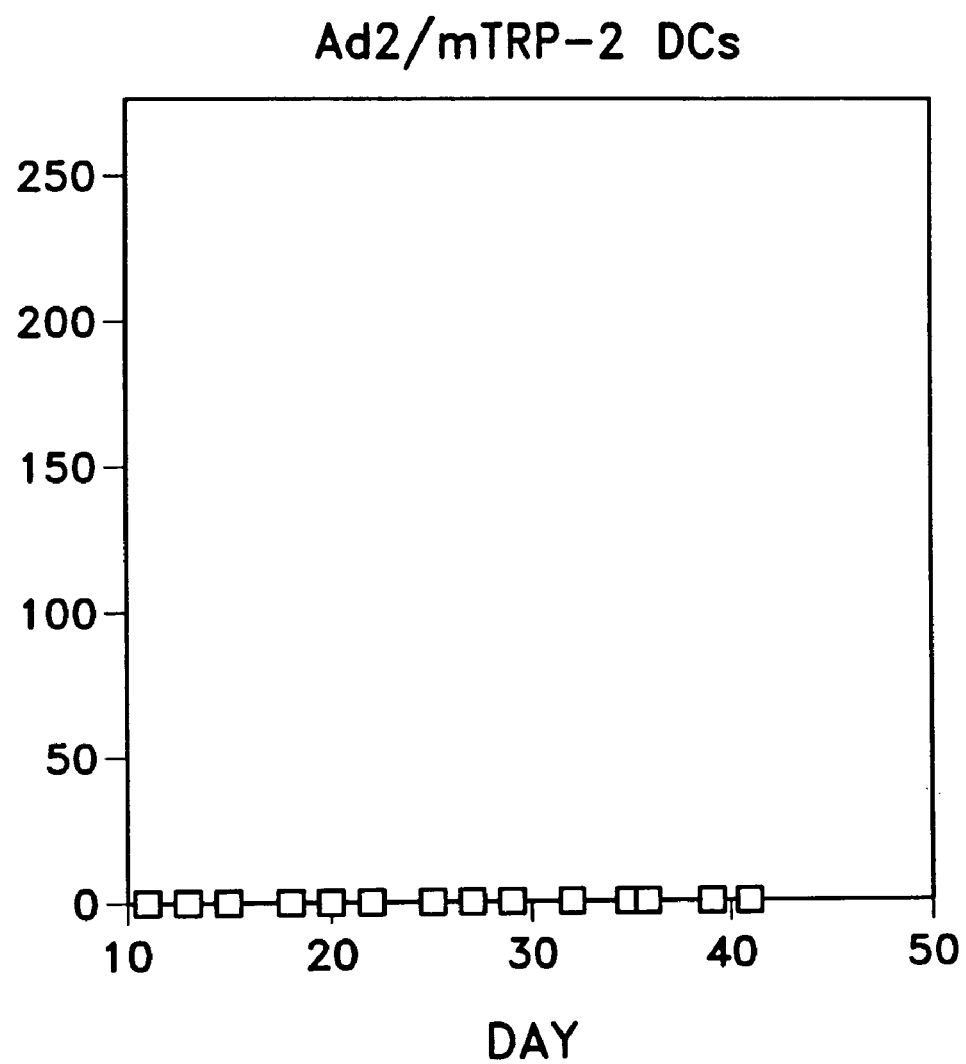

In the pre-immunization model, (See. FIG. 2) DCs are given approximately 2 weeks before challenge with B16 cells to establish immunity and protect against the development of a s.c. tumor or lung metastases. In the more stringent active treatment model, DCs are given 3–4 days after administration of B16 cells to induce host immune responses that will inhibit/prevent ongoing growth of the tumor cells. The efficacy of treatment is assessed by measuring tumor size over time (B16 cells s.c.) or the number of lung metastases (B16 cells i.v.). In addition, levels of TAA-specific immunity (cytotoxic T lymphocytes, antibodies, NK cell lysis) can also be measured.

In both models, autologous DCs from C57BL/6 (H-$2^b$) mice and allogeneic DCs from BALB/c mice (H-$2^d$) are derived from bone marrow as described in section 1 by depletion of all non-DC cell types followed by maturation and growth of DCs in GM-CSF. The DCs are given at a dose of $5\times10^5$ each, either s.c. or i.v.

It is to be understood that while the invention has been described in conjunction with the above embodiments, that the foregoing description and example are intended to illustrate and not limit the scope of the invention. For example, any of the above-noted compositions and/or methods can be combined with known therapies or compositions. Other aspects, advantages and modifications within the scope of the invention will be apparent to those skilled in the art to which the invention pertains.

What is claimed is:

1. A method of inducing an antigen-specific immune response in a subject, comprising co-administering an effective amount of allogeneic and autologous antigen presenting cells (APCs) to the subject, wherein the autologous APCs express an antigen of interest.

2. The method of claim 1, wherein the allogeneic and autologous APCs are dendritic cells.

3. The method of claim 2, wherein the dendritic cells are genetically modified.

4. The method of claim 1, wherein the allogeneic APC is an established, cultured APC.

5. The method of claim 3, wherein the genetic modification comprises introduction of a gene coding for an antigen.

6. The method of claim 1, wherein the antigen is a tumor associated antigen.

7. The method of claim 5, wherein said gene is further comprised in a gene delivery vehicle, wherein the gene delivery vehicle is a retroviral vector, an adenoviral vector, an adeno-associated viral vector or a liposome.

8. The method of claim 1, wherein the APCs are administered intravenously or intradermally to the subject.

9. A method of immunizing a subject, comprising the steps of:
   (i) delivering the antigen of interest to autologous APCs,
   (ii) co-administering an effective amount of allogeneic APCs and the antigen-containing APCs to the subject,
   whereby an antigen-specific immune response is induced in the subject.

10. The method of claim 9, wherein the antigen is delivered to APCs as protein or peptide.

11. A method wherein an antigen-specific response is desired in a subject and the antigen is administered to the subject in an autologous APC, the improvement comprising the delivery of an allogeneic APC.

12. A method of immunizing a subject, comprising the steps of:
   (i) delivering an antigen of interest to autologous antigen presenting cells (APCs),
   (ii) selecting allogeneic APCs capable of inducing an allogeneic reaction on the part of the subject,
   (iii) co-administering an effective amount of the selected allogeneic APCs and the antigen-containing autologous APCs to the subject,
   whereby an antigen-specific immune response is induced in the subject.

* * * * *